(12) United States Patent
Woo et al.

(10) Patent No.: US 7,550,416 B2
(45) Date of Patent: Jun. 23, 2009

(54) PERFUMED HOUSEHOLD PRODUCTS AND METHODS FOR PRESERVING PERFUME INTEGRITY AND EXTENDING FRAGRANCE LIFE

(75) Inventors: Ricky Ah-Man Woo, Hamilton, OH (US); Zaiyou NMN Liu, West Chester, OH (US); Rhonda Jean Jackson, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/100,585

(22) Filed: Apr. 10, 2008

(65) Prior Publication Data

US 2009/0005280 A1    Jan. 1, 2009

Related U.S. Application Data

(63) Continuation-in-part of application No. 12/061,369, filed on Apr. 2, 2008, now abandoned, which is a continuation-in-part of application No. 11/823,293, filed on Jun. 27, 2007, now abandoned.

(51) Int. Cl.
*C11D 3/50* (2006.01)
(52) U.S. Cl. .................................................. 510/102
(58) Field of Classification Search ................ 510/102
See application file for complete search history.

(56) References Cited

U.S. PATENT DOCUMENTS

| | | | |
|---|---|---|---|
| 5,227,366 A * | 7/1993 | Colborn et al. | 512/2 |
| 6,696,395 B1 * | 2/2004 | Woo et al. | 510/101 |
| 6,869,923 B1 * | 3/2005 | Cunningham et al. | 512/4 |
| 2004/0077520 A1 * | 4/2004 | Foley et al. | 512/1 |
| 2004/0097398 A1 * | 5/2004 | Heltovics et al. | 512/3 |
| 2004/0144406 A1 * | 7/2004 | Garabedian et al. | 134/26 |
| 2005/0215459 A1 * | 9/2005 | Policicchio et al. | 510/438 |
| 2006/0014655 A1 * | 1/2006 | Smets et al. | 510/101 |

* cited by examiner

*Primary Examiner*—John R Hardee
(74) *Attorney, Agent, or Firm*—Amy I. Ahn-Roll (57) ABSTRACT

Household cleaning, fabric treatment, or deodorizing products and methods of preserving the integrity of hydrophilic perfume ingredients and extending fragrance life are disclosed. The product and method include an aqueous composition containing a surfactant and a perfume having a substantial proportion of hydrophilic perfume ingredients with a Clog P of less than about 3 and a boiling point greater than about 200° C. The aqueous composition may be contained in plastic containers constructed of hydrophilic perfume compatible materials. The invention preserves perfume integrity by decreasing migration of hydrophilic perfume ingredients into and/or transmission through plastic containers and extends fragrance life once the hydrophilic perfume ingredients are deposited onto a surface.

8 Claims, 2 Drawing Sheets

PERFUMED HOUSEHOLD PRODUCTS AND METHODS FOR PRESERVING PERFUME INTEGRITY AND EXTENDING FRAGRANCE LIFE

CROSS REFERENCE TO RELATED APPLICATION

This application is a Continuation-in-Part of U.S. application Ser. No. 12/061,369, filed Apr. 2, 2008 now abandoned, which is a Continuation in Part of U.S. application Ser. No. 11/823,293, Jun. 27, 2007 now abandoned.

FIELD OF THE INVENTION

The present invention relates to household cleaning, fabric treatment, and deodorizing products that include an aqueous composition having hydrophilic, high molecular weight, perfume ingredients, packaged in a plastic container. The aqueous composition is in a solubilized or emulsified state and contains a substantial proportion of perfume ingredients with a Clog P less than about 3 and a boiling point greater than about 200° C. such that transmission of the perfume ingredients into and/or through the plastic container during storage is minimized and fragrance life, once dispensed from the container, is extended.

BACKGROUND

It is recognized that consumers appreciate household cleaning, fabric treatment and deodorizing products which impart a pleasant fragrance to surfaces treated with these products. For convenience and flexibility in use, it is highly desirable that household cleaning, fabric treatment, and deodorizing compositions be packaged in plastic containers as opposed to, for example, glass containers, or cost reasons, polyethylene is a preferred material for manufacturing plastic containers for such compositions. It has been found, however, that hydrophobic perfume ingredients have a tendency to be lost from the aqueous composition by absorption into and/or transmission through the polyethylene during storage of the composition. This results in a change in the perfume integrity or fragrance characteristics as well as a reduction in the fragrance life which would otherwise be obtained on surfaces treated with the composition. It has also been found that perfume ingredients with low boiling points, which have not been lost during storage, are more quickly lost than perfume ingredients with high boiling points once dispensed from the container.

SUMMARY OF THE INVENTION

The present invention relates to household cleaning fabric treatment, or deodorizing products comprising an aqueous position that includes from about 0.01% to about 50% of a surfactant and from about 0.003% to about 5% of a perfume wherein the perfume contains at least about 10% of one or more hydrophilic perfume ingredients having a Clog P less than about 3 and a boiling point greater than about 200° C., and wherein the composition is contained in a plastic container constructed of at least about 80% hydrophilic perfume compatible materials. In one embodiment of the present invention, the aqueous composition is impregnated in a wet wipe or other substrate for cleaning or deodorizing surfaces.

The present invention also relates to a method of preserving perfume integrity and extending fragrance life in household cleaning, fabric treatment, or deodorizing products by providing an aqueous composition including from about 0.01% to about 50% of a surfactant and from about 0.003% to about 5% of a perfume, wherein the perfume contains at least about 10% of one or more hydrophilic perfume ingredients having a Clog P of less than about 3 and a boiling point greater than about 200° C., and packaging the composition in a plastic container constructed of at least about 80% hydrophilic perfume compatible materials.

BRIEF DESCRIPTION OF THE DRAWINGS

While the specification concludes with the claims particularly pointing and distinctly claiming the invention, it is believed that the present invention will be better understood from the following description taken in conjunction with the accompanying drawings in which:

DETAILED DESCRIPTION OF THE INVENTION

In accordance with the present invention it has been found that when household cleaning, fabric treatment or deodorizing products comprising waters surfactant, and perfumes are packaged in conventional plastic containers, such as those constructed of high density polyethylene (HDPE), there is a tendency for certain perfume ingredients to be lost from the perfume. Without wishing to be bound by any particular theory, it is believed that perfume ingredients are lost by absorption of the hydrophobic perfume ingredients (i.e. those having a Clog P of about 3 or greater) into and/or transmission through the plastic container. When the perfume contains substantial amounts of such hydrophobic perfume ingredients such loss considerably alters the integrity or intended fragrance of the perfume. Containers made of polyethylene terephthalate (PET) or glass do not exhibit a detrimental effect on hydrophobic perfume ingredients. However, consumers prefer plastic containers over glass for safety reasons with glass breaking, and plastic containers are (generally less expensive than glass and PET. Material barriers to lessen the absorption and/or transmission of perfume ingredients into and/or through plastic containers have been considered but added production costs and time make this option undesirable.

It has now been found that the integrity of perfume ingredients can be better preserved in household cleaning fabric treatment, and deodorizing products by utilizing a substantial amount of perfume ingredients that have a Clog P of less than about 3 and packaging the products in plastic containers constructed of at least 80% hydrophilic perfume compatible materials without the addition of material barriers in the plastic containers. The integrity of the perfume ingredients can be further enhanced by utilizing perfume ingredients with a Clog P of less than about 3 and a high boiling point; one that is greater than about 200° C.

The present invention is an household cleaning, fabric treatment or deodorizing product having an aqueous composition comprising, in addition to water, from about 0.01% to about 50% of a surfactant and from about 0.003% to about 5% of a perfume, wherein the perfume contains at least about 10% of one or more hydrophilic perfume ingredients having a Clog P of less than about 3 and a boiling point greater than about 200° C., and wherein the product is contained in a plastic container constructed of at least about 80% hydrophilic perfume compatible materials. In one aspect of the present invention, the aqueous composition is impregnated in a wet wipe or other substrate for cleaning or deodorizing surfaces.

The present invention also includes methods of preserving the integrity of perfume ingredients and extending fragrance life, by providing, the aforesaid household cleaning fabric treatment or deodorizing product.

A. Perfume

The aqueous compositions of the present invention contain perfumes at levels from about 0.003% to about 5%, alternatively from about 0.003% to about 1% alternatively from about 0.01% to about 1%, alternatively from about 0.015% to about 0.5%, alternatively about 0.2% to about 0.4%, alternatively about 0.3% to about 0.4%, alternatively from about 0.05% to about 0.3% alternatively from about 0.05% to about 0.2%, by weight of the composition. The perfumes selected for use in the compositions of the present invention contain ingredients with fragrance characteristics to provide a fresh impression on the surface to which the composition is directed.

Perfumes that are not too hydrophobic provide high initial fragrance impact on surfaces. The less hydrophobic perfume ingredients are more soluble in water, and are more available in the freshening composition. The degree of hydrophobicity of a perfume ingredient can be correlated with its octanol/water partitioning coefficient P. The octanol/water partitioning coefficient of a perfume ingredient is the ratio between its equilibrium concentration in octanol and in water. A perfume ingredient with a greater partitioning coefficient P is more hydrophobic. Conversely, a perfume ingredient with a smaller partitioning coefficient P is more hydrophilic. The perfume ingredients of this invention can have an octanol/water partitioning coefficient P of about 1000 or smaller. Since the partitioning coefficients of the perfume ingredients normally have high values, they are more conveniently given in the from of their logarithm to the base 10, log P.

The log P of many perfume ingredients has been reported; for example, the Pomona 92 database available from Daylight Chemical Information Systems, Inc. (Daylog CIS), Irvine, Calif., contains many, along with citations to the original literature. However, the log P values are most conveniently calculated by the "CLOG P" program also available from Daylight CIS. This program also lists experimental log P values when they are available in the Pomona 92 database. The "calculated log P" (Clog P) is determined by the fragment approach of Hansch and Leo (cf., A. Leo, in Comprehensive Medicinal Chemistry, Vol. 4, C. Hansch. P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity and chemical bonding. The Clog P values, which are the most reliable and widely used estimates for this physicochemical property are used instead of the experimental log P values in the selection of perfume ingredients which are useful in the present invention.

In addition to providing the freshening fragrance to surfaces when first sprayed the aqueous compositions of the present invention contain an effective amount of perfume to provide some lingering fragrance in wear, and some extra fragrance to be released upon rewetting. Fragrance life can be extended by utilizing perfume ingredients with a Clog P of less than about 3 and a boiling point greater than about 200° C. The evaporation rate of a perfume ingredient is inversely proportional to its boiling point; the higher the boiling point of a perfume ingredient, the lower the evaporation rate.

The aqueous compositions of the present invention contain a substantial portion of perfume ingredients (at least about 10%, alternatively at least 40%, alternatively at least 70%) which have a Clog P of less than 3 and a boiling point greater than about 200° C. At least about 10%, alternatively at least about 40%, alternatively at least about 70% by weight of the perfume is composed of perfume ingredients which include aromatic and aliphatic esters having molecular weights from about 130 to about 250; aliphatic and aromatic alcohols having molecular weights from about 90 to about 240; aliphatic ketones having molecular weights from about 150 to about 260; aromatic ketones having molecular weights from about 150 to about 270; aromatic and aliphatic lactones having molecular weights from about 130 to about 290; aliphatic aldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320. The perfume ingredients can be essentially free from nitromusks and halogenated fragrances. Non-limiting examples of suitable perfume ingredients include those listed in Table 1 and mixtures thereof.

TABLE 1

| Perfume Ingredient | Boiling Point (° C.) | Clog P (at 25° C.) |
|---|---|---|
| 2-Cyclohexylethanol | 201.2 | 2.415 |
| Phenylacetaldehyde | 201.3 | 1.784 |
| cis-3-Octen-1-ol | 203.0 | 2.455 |
| 3,3,5-Trimethylcyclohexanol | 203.1 | 2.824 |
| Methyl 2-octynoate | 203.4 | 2.568 |
| Ligustral | 203.6 | 2.361 |
| 3,3-Dimethylcyclohexyl methyl ketone | 203.8 | 2.861 |
| Camphor | 204.2 | 2.177 |
| Stemone | 205.0 | 2.637 |
| Linalool | 205.1 | 2.549 |
| Nerol oxide | 206.7 | 2.412 |
| Methyl phenylacetate | 207.0 | 1.820 |
| Benzyl alcohol | 207.1 | 1.104 |
| Ethyl benzoate | 207.2 | 2.640 |
| Hydratropaldehyde | 207.3 | 2.093 |
| Dimethyl cyclohexene carboxaldehyde | 207.8 | 2.361 |
| 4-Isopropylcyclohexanol | 209.0 | 2.714 |
| Menthone racemic | 209.4 | 2.831 |
| (E)-2,(Z)-6-Nonadienal | 209.5 | 2.681 |
| Benzyl acetate | 210.8 | 1.960 |
| Mugoul | 211.0 | 2.609 |
| Isomenthone | 212.1 | 2.831 |
| 2-sec.Butylcyclohexanone | 213.1 | 2.841 |
| 4-Terpineol | 214.4 | 2.749 |
| Fenchyl alcohol | 214.9 | 2.579 |
| Ocimenol | 215.0 | 2.609 |
| p-Cresyl acetate | 215.3 | 1.990 |
| alpha-Methylbenzyl acetate | 216.1 | 2.269 |
| 1-Borneol | 216.9 | 2.579 |

TABLE 1-continued

| Perfume Ingredient | Boiling Point (° C.) | Clog P (at 25° C.) |
|---|---|---|
| Phenylacetaldehyde dimethyl acetal | 217.1 | 1.293 |
| alpha-Terpineol | 218.0 | 2.629 |
| Allyl amyl glycolate | 218.0 | 2.377 |
| 4-Methylacetophenone | 218.5 | 2.080 |
| p-Anisaldehyde | 219.8 | 1.779 |
| Iso Cyclo Citral | 220.3 | 2.880 |
| Ethyl nicotinate | 221.3 | 1.296 |
| Phenethyl alcohol | 221.7 | 1.183 |
| delta-Nonalactone | 221.9 | 2.802 |
| Terpineol (alpha, beta, gamma) | 222.8 | 2.749 |
| gamma-Nonalactone | 223.9 | 2.772 |
| Benzyl propionate | 224.3 | 2.489 |
| 2,6-nonadienal | 224.7 | 2.500 |
| Ethyl phenylacetate | 225.5 | 2.349 |
| Citral | 225.6 | 2.950 |
| Hydratopic alcohol | 226.4 | 1.582 |
| Methoxycitronellal | 226.8 | 2.117 |
| Linalool oxide | 228.0 | 1.964 |
| Isopulegol | 229.8 | 2.749 |
| 3-Phenylbutanal | 230.1 | 2.122 |
| Cuminaldehyde | 230.2 | 2.922 |
| Dimethyl benzyl carbinol | 230.8 | 1.891 |
| L-Carvone | 231.9 | 2.013 |
| 2-Phenylethyl acetate | 232.7 | 2.129 |
| Benzylacetone | 234.7 | 1.739 |
| Acetanisole | 234.8 | 1.801 |
| Citral dimethyl acetal | 235.0 | 2.879 |
| Benzyl isobutyrate | 235.8 | 2.798 |
| Methyl salicylate | 235.8 | 2.445 |
| Dimethyl anthranilate | 236.0 | 2.161 |
| Nerol | 237.4 | 2.769 |
| trans-Geraniol | 237.4 | 2.769 |
| p-Cresyl isobutyrate | 237.7 | 2.828 |
| Livescone | 237.7 | 2.627 |
| 1-(Prop-2-enoxy) 2-phenylethane | 238.3 | 2.333 |
| Voiliff | 238.4 | 2.767 |
| Decahydro-2-naphthol | 238.6 | 2.699 |
| Methyl anthranilate | 241.6 | 2.024 |
| Hydrocinnamyl alcohol | 242.0 | 1.712 |
| 2-Phenoxyethanol | 242.1 | 1.188 |
| 2,3-Benzopyrrole | 242.1 | 2.132 |
| Maltol | 242.7 | 0.150 |
| Cinnamic aldehyde | 243.3 | 1.899 |
| Methyl cinnamate | 244.3 | 2.465 |
| Jasmolactone | 244.8 | 2.847 |
| Dihydrocoumarin | 245.3 | 1.476 |
| Flor Acetate | 245.9 | 2.357 |
| Dimethyl benzyl carbinyl acetate | 246.4 | 2.837 |
| 1,5-Dimethyl-bicyclo[3.2.1]octan-8-one, oxime- | 246.8 | 2.547 |
| Ethyl maltol | 247.8 | 0.679 |
| Hydroxycitronellal | 248.0 | 1.541 |
| Eugenyl methyl ether | 251.5 | 2.673 |
| Acetaldehyde ethyl phenylethyl acetal | 253.2 | 2.351 |
| Benzyl-tert-butanol | 253.7 | 2.420 |
| Phenethyl isobutyrate | 254.7 | 2.967 |
| Anisyl acetate | 256.1 | 1.879 |
| Cinnamic alcohol | 256.1 | 1.408 |
| 6-Methylquinoline | 256.3 | 2.528 |
| Allyl phenoxyacetate | 257.2 | 2.253 |
| Frutene | 257.4 | 2.886 |
| Veratraldehyde | 257.6 | 1.240 |
| Hydroxycitronellal dimethyl acetal | 259.3 | 1.640 |
| Dihydroeugenol | 259.7 | 2.881 |
| Cinnamyl acetate | 260.4 | 2.354 |
| Ethyl cinnamate | 261.1 | 2.994 |
| Phenoxyethyl propionate | 262.7 | 2.614 |
| Eugenol | 263.3 | 2.397 |
| Heliotropin | 263.5 | 1.138 |
| Cinnamyl nitrile | 266.4 | 1.959 |
| exo-2-Camphanyl beta-hydroxyethyl ether | 267.3 | 2.597 |
| Ethyl 3-phenylglycidate | 267.5 | 2.195 |
| Coumarin | 268.5 | 1.412 |
| Scentenal | 269.6 | 0.924 |
| Anisylpropanal | 270.0 | 1.951 |
| Isoeugenol | 270.3 | 2.577 |
| Methyl lavender ketone | 270.7 | 2.413 |
| 2-Phenoxyethyl isobutyrate | 271.8 | 2.923 |
| Vanillin | 272.2 | 1.275 |
| Acetaldehyde phenylethyl propyl acetal | 274.6 | 2.880 |
| Jasmal | 275.7 | 2.379 |
| Ethyl methylphenylglycidate | 276.5 | 2.714 |
| Ethyl vanillin | 286.1 | 1.804 |
| Isoeugenyl acetate | 286.6 | 2.283 |
| Heliotropine diethyl acetal | 288.3 | 2.062 |
| 2H-1,5-Benzodioxepin-3(4H)-one, 7-methyl- | 301.1 | 1.803 |
| 4-(4-Hydroxyphenyl)butanone-2 | 301.2 | 1.072 |
| Vanillin isobutyrate | 301.9 | 1.508 |
| Helional | 301.9 | 1.387 |
| Cashmeran | 302.4 | 2.373 |
| Piperonyl acetone | 307.3 | 1.094 |
| Methyl beta-naphthyl ketone | 310.6 | 2.755 |
| Methyl dihydrojasmonate | 314.3 | 2.419 |
| Lyral | 319.8 | 2.150 |

In another embodiment, the aqueous compositions of the present invention include perfume ingredients that have a Clog P of less than about 3 and a boiling point greater than about 250° C. Non-limiting, exemplary perfume ingredients of this type include those in Table 2 and mixtures thereof.

TABLE 2

| Perfume Ingredient | Boiling Point (° C.) | Clog P (at 25° C.) |
|---|---|---|
| Eugenyl methyl ether | 251.5 | 2.673 |
| Acetaldehyde ethyl phenylethyl acetal | 253.2 | 2.351 |
| Benzyl-tert-butanol | 253.7 | 2.420 |
| Phenethyl isobutyrate | 254.7 | 2.967 |
| Anisyl acetate | 256.1 | 1.879 |
| Cinnamic alcohol | 256.1 | 1.408 |
| 6-Methylquinoline | 256.3 | 2.528 |
| Allyl phenoxyacetate | 257.2 | 2.253 |
| Frutene | 257.4 | 2.886 |
| Veratraldehyde | 257.6 | 1.240 |
| Hydroxycitronellal dimethyl acetal | 259.3 | 1.640 |
| Dihydroeugenol | 259.7 | 2.881 |
| Cinnamyl acetate | 260.4 | 2.354 |
| Ethyl cinnamate | 261.1 | 2.994 |
| Phenoxyethyl propionate | 262.7 | 2.614 |
| Eugenol | 263.3 | 2.397 |
| Heliotropin | 263.5 | 1.138 |
| Cinnamyl nitrile | 266.4 | 1.959 |
| exo-2-Camphanyl beta-hydroxyethyl ether | 267.3 | 2.597 |
| Ethyl 3-phenylglycidate | 267.5 | 2.195 |
| Coumarin | 268.5 | 1.412 |
| Scentenal | 269.6 | 0.924 |
| Anisylpropanal | 270.0 | 1.951 |
| Isoeugenol | 270.3 | 2.577 |
| Methyl lavender ketone | 270.7 | 2.413 |
| 2-Phenoxyethyl isobutyrate | 271.8 | 2.923 |
| Vanillin | 272.2 | 1.275 |
| Acetaldehyde phenylethyl propyl acetal | 274.6 | 2.880 |
| Jasmal | 275.7 | 2.379 |
| Ethyl methylphenylglycidate | 276.5 | 2.714 |
| Ethyl vanillin | 286.1 | 1.804 |
| Isoeugenyl acetate | 286.6 | 2.283 |
| Heliotropine diethyl acetal | 288.3 | 2.062 |
| 2H-1,5-Benzodioxepin-3(4H)-one, 7-methyl- | 301.1 | 1.803 |
| 4-(4-Hydroxyphenyl)butanone-2 | 301.2 | 1.072 |
| Vanillin isobutyrate | 301.9 | 1.508 |
| Helional | 301.9 | 1.387 |
| Cashmeran | 302.4 | 2.373 |
| Piperonyl acetone | 307.3 | 1.094 |
| Methyl beta-naphthyl ketone | 310.6 | 2.755 |

TABLE 2-continued

| Perfume Ingredient | Boiling Point (° C.) | Clog P (at 25° C.) |
|---|---|---|
| Methyl dihydrojasmonate | 314.3 | 2.419 |
| Lyral | 319.8 | 2.150 |

In another embodiment, perfume ingredients with a Clog P of less than about 3 and a boiling point greater than about 280° C. are used in the present invention. Non-limiting, exemplary perfume ingredients of this type include those in Table 3 and mixtures thereof.

TABLE 3

| Perfume Ingredient | Boiling Point (° C.) | Clog P (at 25° C.) |
|---|---|---|
| Ethyl vanillin | 286.1 | 1.804 |
| Isoeugenyl acetate | 286.6 | 2.283 |
| Heliotropine diethyl acetal | 288.3 | 2.062 |
| 2H-1,5-Benzodioxepin-3(4H)-one, 7-methyl- | 301.1 | 1.803 |
| 4-(4-Hydroxyphenyl)butanone-2 | 301.2 | 1.072 |
| Vanillin isobutyrate | 301.9 | 1.508 |
| Helional | 301.9 | 1.387 |
| Cashmeran | 302.4 | 2.373 |
| Piperonyl acetone | 307.3 | 1.094 |
| Methyl beta-naphthyl ketone | 310.6 | 2.755 |
| Methyl dihydrojasmonate (e.g.Hedione) | 314.3 | 2.419 |
| Lyral | 319.8 | 2.150 |

When cyclodextrin is added to the aqueous compositions of the present invention, the perfume to cyclodextrin weight ratio is typically from about 3:100 to about 100:100 alternatively from about 4:100 to about 50:100 alternatively from about 5:100 to about 40:100 alternatively from about 5:100 to about 25:100 alternatively from about 1:8 to about 1:4.

B. Surfactants

Surfactants that are suitable for use in the aqueous compositions of the present invention can be any of those suitable for use in household cleaning, fabric treatment or deodorizing compositions. These include anionic nonionic, cationic, ampholytic and zwitterionic detergents.

Examples of anionic detergents include $C_8$-$C_{22}$ alkyl sulfates, alkylbenzene sulfonates having from 9 to 15 carbon atoms in the alkyl group alkyl ethyleneoxide ether sulfates having from 8-22 carbon atoms in the alkyl chain and from 1 to 30 ethylene oxide groups, and $C_8$ to $C_{22}$ fatty acid soaps. Examples of nonionic surfactants include condensates of from 3 to 30 mmoles of ethylene oxide with an aliphatic alcohol of 8 to 22 carbon atoms, condensates of 5 to 30 moles of ethylene oxide with an alkyl phenol wherein the alkyl contains 9 to 15 carbon atoms and $C_8$ to $C_{22}$ alkyl dimethyl amine oxides. In one embodiment, the nonionic surfactant is a secondary alcohol ethoxylate known as Tergitol™ 15-S, available from The Dow Chemical Company. Examples of ampholytic and zwitterionic surfactants are found in U.S. Pat. No. 3,929,678, Laughlin et al., issued Dec. 30, 1975 at Col, 19, line 38 through Col. 22 line 48. Examples of cationic surfactants are tetraalkyl quaternary ammonium salts having at least one alkyl chain of 8 to 22 carbon atoms, wherein the other alkyl groups can contain from 1 to 22 carbon atoms and wherein the anionic counterion is halogen ethylsulfate or methylsulfate. The term "household cleaning and fabric treatment and deodorizing compositions" herein includes fabric laundering, softening and freshening compositions, and floor, rug and other household surface treatment compositions where it is desired to clean and/or impart a beneficial treatment or property to the surface. Surfactants may be used at levels of from about 0.01% to about 50%, alternatively from about 0.01% to about 30%, alternatively from about 0.01% to about 20%, alternatively from about 0.01% to about 10%, alternatively from about 0.05% to about 6%, alternatively from about 0.08% to about 2%, by weight of the aqueous composition, depending on the intended usage of the product. Typical levels may be from 0.1% to 30% and 5% to 20%. Additional surfactants are disclosed in U.S. Pat. No. 3,664,961 to Norris, issued May 23, 1972.

C. Optional Ingredients

The aqueous compositions of the present invention can also contain the usual adjuvants found in such compositions. These include builders (e.g. phosphates, citrates polycarboxylates, silicates, etc.), soil suspending agents (e.g. carboxymethyl cellulose, antimicrobial agents (e.g. cyclohexidine, biguanides, etc.) hydrotropes (e.g. sodium cumene sulfonate, propylene glycol) chelating agents (e.g. Versenne 100, available from The Dow Chemical Company) enzymes (e.g. proteases) preservatives and solvents (e.g. ethanol, ethylene glycol monobutyl ether).

In addition to the perfume ingredients which have a Clog P less than about 3, the perfume can contain perfume ingredients which have a Clog P greater than about 3. Non-limiting examples of such ingredients are shown in Table 4.

TABLE 4

| Perfume Ingredients | Clog P |
|---|---|
| Dihydro myrcenol | 3.03 |
| Isononyl alcohol | 3.08 |
| Citronellol | 3.25 |
| Tetrahydro linalool | 3.52 |
| Terpinyl acetate | 3.58 |
| Geranyl acetate | 3.72 |
| Phenyl ethyl phenyl acetate | 3.77 |
| Lilial (P.T. Bucinal) | 3.86 |
| Gamma methyl ionone | 4.02 |
| Vertenex | 4.06 |
| Diphenyl methane | 4.06 |
| p'Cymene | 4.07 |
| Alpha pinene | 4.18 |
| Benzyl salicylate | 4.21 |
| d-Limonene | 4.35 |
| Cis-hexenyl salicylate | 4.61 |
| Hexyl cinnamic aldehyde | 4.85 |
| Hexyl cinnamic aldehyde | 4.85 |
| Cedryl acetate | 5.48 |
| Phentolide | 5.98 |
| Tonalid | 6.25 |

Compositions herein which have good deodorizing effect on surfaces (e.g. fabrics carpets, counter tops, etc.) can contain cyclodextrin. In addition to the perfume providing the desired fragrance to the treated surface cyclodextrin has the ability to absorb odors such as those present in perspiration and urine.

The cyclodextrins used in the present invention can be highly water-soluble such as, alpha-cyclodextrin and for derivatives thereof, gamma-cyclodextrin and/or derivatives thereof derivatised beta-cyclodextrins, and/or mixtures thereof. The derivatives of cyclodextrin consist mainly of molecules wherein some of the OH groups are converted to OR groups. Cyclodextrin derivatives include, e.g. those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins wherein R is a —CH$_2$—CH(OH)—CH$_3$ or a —CH$_2$CH$_2$—OH group; branched cyclodextrins such as maltose-bonded cyclodextrins; cationic cyclodextrins such as those containing 2-hydroxy-3-(dimethylamino)propyl ether, wherein R is CH$_2$—CH(OH)—CH$_2$—N(CH$_3$)$_2$ which is cationic at low pH; quaternary ammonium, e.g., 2-hydroxy-3-(trimethylammonio)propyl ether chloride groups, wherein R is CH$_2$—CH(OH) —CH$_2$—N$^+$(CH$_3$)$_3$Cl$^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F, Diedaini-Pilard and B. Perly, The 7th International Cyclodextrin Symposium Abstracts, April 1994, p. 49, said references being incorporated herein by reference; and mixtures thereof. Other cyclodextrin derivatives are disclosed in U.S. Pat. Nos. 3,426,011, 3,453,257, 3,453,258, 3,453,259, and 3,453,260, all in the names of Parmerter et al., and all issued Jul. 1, 1969; U.S. Pat. No. 3,459,731 to Gramera et al., issued Aug. 5, 1969; U.S. Pat. No. 3,553,191 to Parmerter et al., issued Jan. 5, 1971; U.S. Pat. No. 3,565,887 to Parmerter et al., issued Feb. 23, 1971; U.S. Pat. No. 4,535,152 to Szejtli et al., issued Aug. 13, 1985; U.S. Pat. No. 4,616,008 to 1 Hirai et al., issued Oct. 7, 1986; U.S. Pat. No. 4,678,598 to Ogino et al., issued Jul. 7, 1987; U.S. Pat. No. 4,638,058 to Brandt et al., issued Jan. 20, 1987; and U.S. Pat. No. 4,746,734 to Tsuchiyama et al., issued May 24, 1988; all of said patents being incorporated herein by reference.

Highly water-soluble cyclodextrins are those having water solubility of at least about 10 g in 100 ml of water at room temperature, alternatively at least about 20 g in 100 ml of water, alternatively at least about 25 g in 100 ml of water at room temperature. The availability of solubilized, uncomplexed cyclodextrins is essential for effective and efficient odor control performance. Solubilized water-soluble cyclodextrin can exhibit more efficient odor control performance than non-water-soluble cyclodextrin when deposited onto surfaces, especially fabric.

Examples of water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin. Hydroxyalkyl cyclodextrin derivatives can have a degree of substitution of from about 1 to about 14, alternatively from about 1.5 to about 7, wherein the total number of OR groups per cyclodextrin is defined as the degree of substitution. Methylated cyclodextrin derivatives typically have a degree of substitution of from about 1 to about 18, alternatively from about 3 to about 16. A known methylated beta-cyclodextrin is heptakis-2,6-di-O-methyl-β-cyclodextrin, commonly known as DIMEB, in which each glucose unit has about 2 methyl groups with a degree of substitution of about 14. A more commercially available methylated beta-cyclodextrin is a randomly methylated beta-cyclodextrin, commonly known as RAMEB having different degrees of substitution normally of about 12.6. DIMEB affects the surface activity of the surfactants more than RAMEB. Cyclodextrins are available from Cerestar USA, Inc. and Wacker Chemicals (USA), Inc.

A mixture of cyclodextrins can be used in the present invention. The amount of cyclodextrins used in the compositions can range from about 0.01% to about 20% by weight of the aqueous composition. If the composition is intended to be diluted before use it will contain from about 3% to about 20%, alternatively about 5% to about 10%. Compositions intended to be used in undiluted form will generally contain from about 0.01% to about 5%, alternatively about 0.1% to about 3%, alternatively about 0.5% to about 2%.

When formulating compositions with cyclodextrins, surfactants which have especially good compatibility with cyclodextrin can be used. Suitable cyclodextrin-compatible surfactants can be readily identified by the absence of effect of cyclodextrin on the surface tension provided by the surfactant. This is achieved by determining the surface tension (in dyne/cm$^2$) of aqueous solutions of the surfactant in the presence and in the absence of 1% of a specific cyclodextrin in the solutions. The aqueous solutions contain surfactant at concentrations of approximately 0.5%, 0.1%, 0.01%, and 0.005%. The cyclodextrin can affect the surface activity of a surfactant by elevating the surface tension of the surfactant solution. If the surface tension at a given concentration in water differs by more than about 10% from the surface tension of the same surfactant in the 1% solution of the cyclodextrin that is an indication of a strong interaction between the surfactant and the cyclodextrin. The surfactants herein can have a surface tension in an aqueous solution that is different (lower) by less than about 10%, alternatively less than about 5% and alternatively less than about 1% from that of the same concentration solution containing 1% cyclodextrin.

(a) Block Copolymers

Non-limiting examples of cyclodextrin-compatible nonionic surfactants include block copolymers of ethylene oxide and propylene oxide. Suitable block polyoxyethylene-polyoxypropylene polymeric surfactants that are compatible with most cyclodextrins include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as C$_{12-18}$ aliphatic alcohols are not generally compatible with the cyclodextrin. Certain of the block polymer surfactant compounds designated Pluronic® and Tetronic® by the BASF-Wyandotte Corp., Wyandotte, Mich., are read available.

Non-limiting examples of cyclodextrin-compatible surfactants of this type include: Pluronic Surfactants with the general formula H(EO)$_n$(PO)$_m$(EO)$_n$H, wherein EO is an ethylene oxide group, PO is a propylene oxide group, and n and m are numbers that indicate the average number of the groups in the surfactants. Typical examples of cyclodextrin-compatible pluronic surfactants are:

| Name  | Average MW | Average n | Average m |
|-------|------------|-----------|-----------|
| L-101 | 3,800      | 4         | 59        |
| L-81  | 2,750      | 3         | 42        |
| L-44  | 2,200      | 10        | 23        |
| L-43  | 1,850      | 6         | 22        |
| F-38  | 4,700      | 43        | 16        |
| P-84  | 4,200      | 19        | 43,       | and mixtures thereof.

Tetronic Surfactants with the general formula:

wherein EO, PO, n, and m have the same meanings as above. Typical examples of cyclodextrin-compatible tetronic surfactants are:

| Name | Average MW | Average n | Average m |
|---|---|---|---|
| 901 | 4,700 | 3 | 18 |
| 908 | 25,000 | 114 | 22, | and mixtures thereof.

"Reverse" Pluronic and Tetronic surfactants have the following general formulas:

Reverse Pluronic Surfactants $H(PO)_m(EO)_n(PO)_m H$

Reverse Tetronic Surfactants wherein EO, PO n, and m have the same meanings as above. Typical examples of cyclodextrin-compatible reverse pluronic and reverse tetronic surfactants are:

Reverse Pluronic surfactants:

| Name | Average MW | Average n | Average m |
|---|---|---|---|
| 10 R5 | 1,950 | 8 | 22 |
| 25 R1 | 2,700 | 21 | 6 |

Reverse Tetronic surfactants

| Name | Average MW | Average n | Average m |
|---|---|---|---|
| 130 R2 | 7,740 | 9 | 26 |
| 70 R2 | 3,870 | 4 | 13 | and mixtures thereof (b) Siloxane Surfactants

Another class of cyclodextrin-compatible nonionic surfactants are the polyalkyleneoxide polysiloxanes having a dimethyl polysiloxane hydrophobic moiety and one or more hydrophilic polyalkylene side chains and have the general formula:

$$R^1—(CH_3)_2SiO—[(CH_3)_2SiO]_a—[(CH_3)(R^1)SiO]_b—Si(CH_3)_2—R^1$$

wherein a+b are from about 1 to about 50, alternatively from about 3 to about 30 alternatively from about 10 to about 25 and each $R^1$ is the same or different and is selected from the group consisting of methyl and a poly(ethyleneoxide/propyleneoxide) copolymer group having the general formula:

$$—(CH_2)_nO(C_2H_4O)_c(C_3H_6O)_dR^2$$

with at least one $R^1$ being a poly(ethyleneoxide/propyleneoxide) copolymer group, and wherein n is 3 or 4, alternatively 3; total c (for all polyalkyleneoxy side groups) has a value of from about 1 to about 100, alternatively from about 6 to about 100; total d is from 0 to about 14, alternatively from 0 to about 3; and alternatively d is 0; total c+d has a value of from about 5 to about 150, alternatively from about 9 to about 100 and each $R^2$ is the same or different and is selected from the group consisting of hydrogen, an alkyl having 1 to 4 carbon atoms, and an acetyl group alternatively hydrogen and methyl group.

Examples of this type of surfactant are the Silwet® Hydrostable 68, 611, and 212 available from Momentive Performance Materials. Other representative Silwet surfactants are as follows.

| Name | Average MW | Average a + b | Average total c |
|---|---|---|---|
| L-7608 | 600 | 1 | 9 |
| L-7607 | 1,000 | 2 | 17 |
| L-77 | 600 | 1 | 9 |
| L-7605 | 6,000 | 20 | 99 |
| L-7604 | 4,000 | 21 | 53 |
| L-7600 | 4,000 | 11 | 68 |
| L-7657 | 5,000 | 20 | 76 |
| L-7602 | 3,000 | 20 | 29 |

The molecular weight of the polyalkyleneoxy group ($R^1$) is less than or equal to about 10,000. Alternatively, the molecular weight of the polyalkyleneoxy group is less than or equal to about 8,000, and alternatively ranges from about 300 to about 5,000. Thus, the values of C and d can be those numbers which provide molecular weights within these ranges. However, the number of ethyleneoxy units ($—C_2H_4O$) in the polyether chain ($R^1$) must be sufficient to render the polyalkyleneoxide polysiloxane water dispersible or water soluble. If propyleneoxy groups are present in the polyalkylenoxy chain, they can be distributed randomly in the chain or exist as blocks. Besides surface activity, polyalkyleneoxide polysiloxane surfactants can also provide other benefits, such as antistatic benefits, lubricity and softness to fabrics.

The preparation of polyalkyleneoxide polysiloxanes is well known in the art. Polyalkyleneoxide polysiloxanes of the present invention can be prepared according to the procedure set forth in U.S. Pat. No. 3,299,112, incorporated herein by reference. Typically polyalkyleneoxide polysiloxanes of the surfactant blend of the present invention are readily prepared by an addition reaction between a hydrosiloxane (i.e. a siloxane containing silicon-bonded hydrogen) and an alkenyl ether (e.g., a vinyl, allyl, or methallyl ether) of an alkoxy or hydroxy end-blocked polyalkylene oxide). The reaction conditions employed in addition reactions of this type are well known in the art and in general involve heating the reactants (e.g., at a temperature of from about 85° C. to 110° C.) in the presence of a platinum catalyst (e.g., chloroplatinic acid) and a solvent (e.g., toluene).

(c) Anionic Surfactants

Non-limiting examples of cyclodextrin-compatible anionic surfactants are the alkyldiphenyl oxide disulfonate, having the general formula:

wherein R is an alkyl group. Examples of this type of surfactants are available from the Dow Chemical Company under the trade name Dowfax® wherein R is a linear or branched $C_6$-$C_{16}$ alkyl group. An example of these cyclodextrin-compatible anionic surfactant is Dowfax 3B2 with R being approximately a linear $C_{10}$ group. These anionic surfactants are alternatively not used when the antimicrobial active or preservative etc., is cationic to minimize the interaction with the cationic actives, since the effect of both surfactant and active are diminished.

The surfactants above are either weakly interactive with cyclodextrin (less than 5% elevation in surface tension or non-interactive (less than 1% elevation in surface tension). Normal surfactants like sodium dodecyl sulfate and dodecanolpoly(6)ethoxylate are strongly interactive, with more than a 10% elevation in surface tension in the presence of a typical cyclodextrin like hydroxypropyl beta-cyclodextrin and methylated beta-cyclodextrin.

Typical levels of cyclodextrin-compatible surfactants in aqueous compositions of the present invention are from about 0.01% to about 2%, alternatively from about 0.03% to about 0.6%, alternatively from about 0.05% to about 0.3) %, by weight of the composition. Typical levels of cyclodextrin-compatible surfactants in concentrated compositions are from about 0.1% to about 8%, alternatively from about 0.2% to about 4%, alternatively from about 0.3. % to about 3% by weight of the concentrated composition.

Deodorizing compositions containing cyclodextrin are more fully described in U.S. Pat. No. 6,767,507.

D. Wipes

The aqueous compositions of the present invention may be impregnated into a commercially available substrate such as the substrates discussed in US RE38505, US RE38105, and U.S. Pat. No. 6,936,330, all of which are incorporated herein by reference. In one embodiment, the substrate may be a non-woven, wet-wipe for deodorizing, disinfecting, or cleaning multiple surfaces including inanimate household surfaces.

E. Packaging Container

The aqueous compositions of the present invention can be contained in plastic containers constructed of hydrophilic perfume compatible materials. These materials avoid complexing, with hydroplilic perfume ingredients, such that absorption by and/or transmission through plastic containers is minimized. Suitable hydrophilic perfume compatible materials can be readily identified by determining the average hydrophilic perfume loss through gas chromatography analysis. Hydrophilic perfume compatible materials result in an average hydrophilic perfume ingredient loss of less than about 50% alternatively less than about 20%, alternatively less than about 15% and alternatively less than about 10% of the originally present individual hydrophilic perfume ingredients.

Aqueous compositions containing a substantial amount of hydrophilic perfume ingredients can be stored in plastic container constructed of at least 80% hydrophilic perfume compatible materials for 8 weeks at ambient temperature. After storage, gas chromatography analysis is used to determine the amount of the various perfume ingredients remaining in the aqueous composition and approximate loss is calculated based on the amount of each ingredient originally present.

An effective amount of hydrophilic perfume compatible materials suitable for the present invention is at least about 80%, alternatively about 80% to about 100%, alternatively about 90% to about 100%, and alternatively 100%, by weight of the container. Non-limiting examples of hydrophilic perfume compatible materials are any resins of high density polyethylene (HDPE), low density polyethylene (LDPE), polyvinyl chloride (PVC), polypropylene (PP), polystyrene (PS), polyethylene-co-vinyl alcohol (EVOH), fluorinated polymer such as Aclar®, acrylonitrile-methyl acrylate copolymer such as Barex®, or mixtures thereof. Alternatively HDPE is utilized in the present invention.

In one embodiment, an HDPE bottle, from Plastipak Packaging Inc. Champaign, Ill., is used to contain the aqueous composition of the present invention. HDPE bottles can be made by any blow molding, injection molding, and thermoform process known in the art. For example, for blow molded bottles, heat softened HDPE is extruded as a hollow tube into a mold cavity and forced by pressurized air against the walls of the cold mold cavity to form the bottle. The bottle solidifies by cooling.

It has been found that the perfume compositions having a Clog P of less than about 3 are not fully absorbed into and/or transmitted through the hydrophilic perfume compatible materials such as PP and HDPE. Thus, this assists in preventing transmission of perfume ingredients through plastic containers; which in turn provides consumer noticeable longer lasting fragrance life.

Any of the hydrophilic perfume compatible materials can be used in conjunction with one or more barrier materials including amorphous carbon, silicone oxide or mixtures thereof and metallized coating. The following examples are presented for illustrative purposes, and are not intended, in any way, to limit the scope of the invention.

EXAMPLE I

In this example, two deodorizing compositions for inanimate surfaces (e.g. rugs clothing, counter tops, etc.) are evaluated in 800 ml plastic bottles, constructed of 52 g of HDPE (100% by weight of the bottle) for preserving perfume integrity or minimizing loss of fragrance. The first composition, Composition A, is approximately 0.05% perfume, made up of at least about 47.9% perfume ingredients having a Clog P less than about 3 and a boiling point greater than about 280° C. The second composition, Composition B, is approximately 0.05% perfume, made up of 40.8% perfume ingredients having a Clog P greater than about 3 and a boiling point greater than about 280° C. The control perfume is approximately 0.05% perfume of which 18.7% are perfume ingredients having a Clog P of less than 3 and a boiling point greater than about 280° C.

Panelists evaluate the freshly made and aged compositions (A, B, and Control) for their respective fragrance intensities after the following intervals: immediately after the compositions are sprayed onto fabric, at 2 hours, at 24 hours, and at 48 hours. The freshly made compositions are those that are evaluated immediately after being made or within about two weeks of being properly stored in a 4° C. constant temperature, constant humidity (CTCH) room. The aged compositions are those that have been subject to ambient temperatures or a 49° C. room for about two weeks or more.

Figure 1:
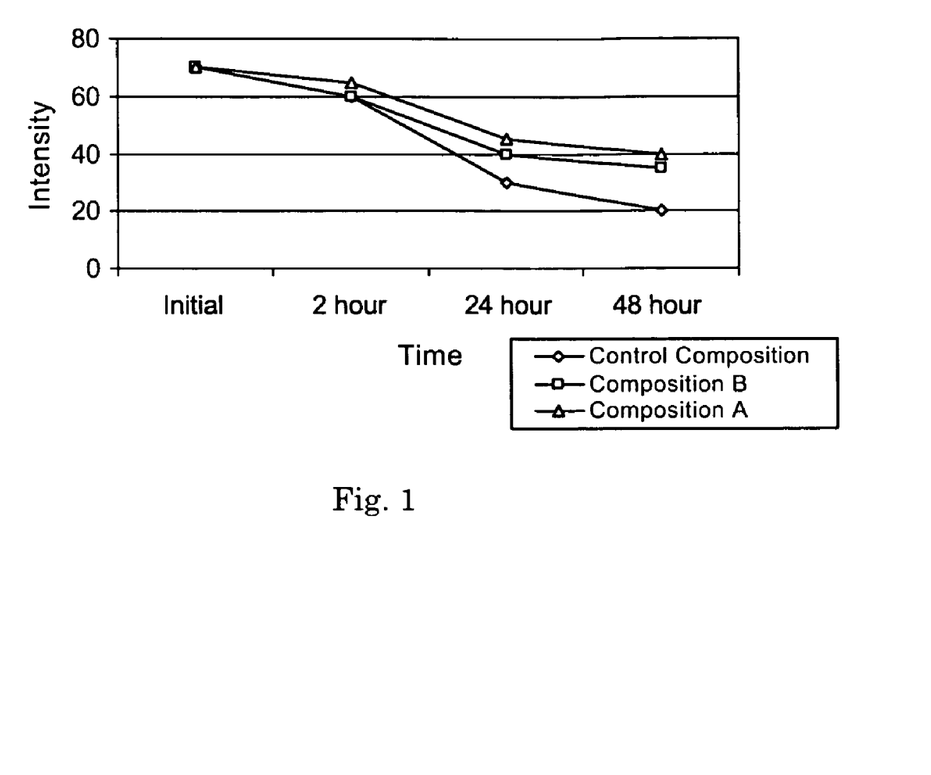
FIG. 1 is a line graph illustrating the fragrance intensity over time of a first embodiment of three fresh perfume compositions over time (the compositions include a control perfume composition and two perfume compositions made in accordance with the present invention)

FIG. 1 and Table 5 show the fragrance intensity of the fresh compositions over time. At 48 hours, Composition A shows a grade of 40, Composition B shows a grade of 35, and the Control composition shows a grade of 20 at 48 hours.

TABLE 5

| FRESH PERFUME | Wet fabric | 2 hour Dry | 24 hour Dry | 48 hour Dry |
|---|---|---|---|---|
| Control Composition | 70 | 60 | 30 | 20 |
| Composition B | 70 | 60 | 40 | 35 |
| Composition A | 70 | 65 | 45 | 40 |

Figure 2:
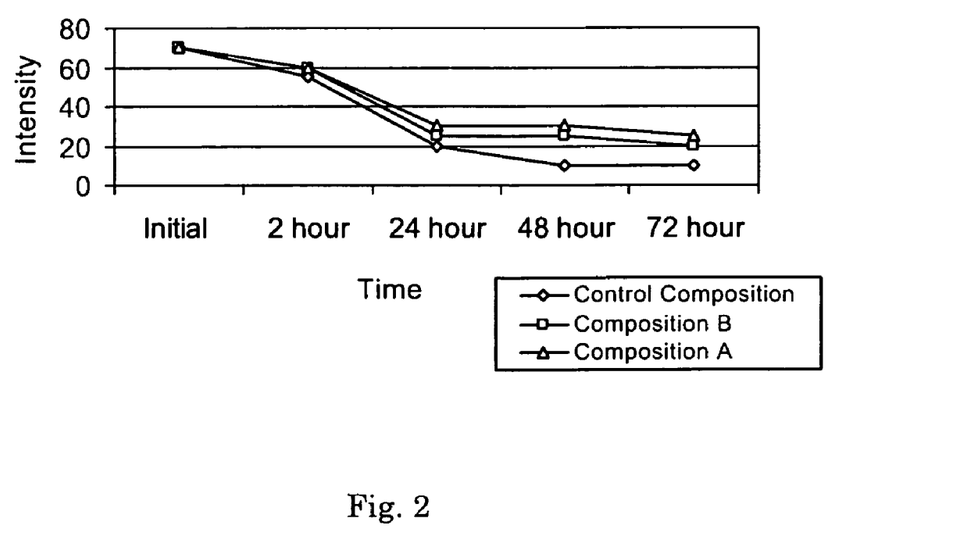
FIG. 2 is a line graph illustrating the fragrance intensity over time of the same three perfumes illustrated in FIG. 1 but aged (subject to ambient temperatures or a 49° C. room for about two weeks or more)

FIG. 2 and Table 6 show the fragrance intensity of the aged compositions on fabric over time. At 48 hours, Composition A shows a grade of 25, Composition B shows a grade of 20 and the Control Composition shows a grade of 10. The difference between consumer noticeable fragrance and fragrance that is not consumer noticeable is a grade of at least 15. In the aged products, the control is not consumer noticeable but Compositions A and B are consumer noticeable.

TABLE 6

| AGED PERFUME | Wet fabric | 2 hour Dry | 24 hour Dry | 48 hour Dry | 72 hour Dry |
|---|---|---|---|---|---|
| Control Composition | 70 | 55 | 20 | 10 | 10 |
| Composition B | 70 | 60 | 25 | 25 | 20 |
| Composition A | 70 | 60 | 30 | 30 | 25 |

Overall, perfume intensity of Composition A and Composition B are retained after 48 hours from when the perfumes are sprayed onto fabric. At 48 hours, perfume character comments included "distinct citrus" for Composition A and "distinct citrus freshness" for Composition B.

EXAMPLE II

Figure 3:
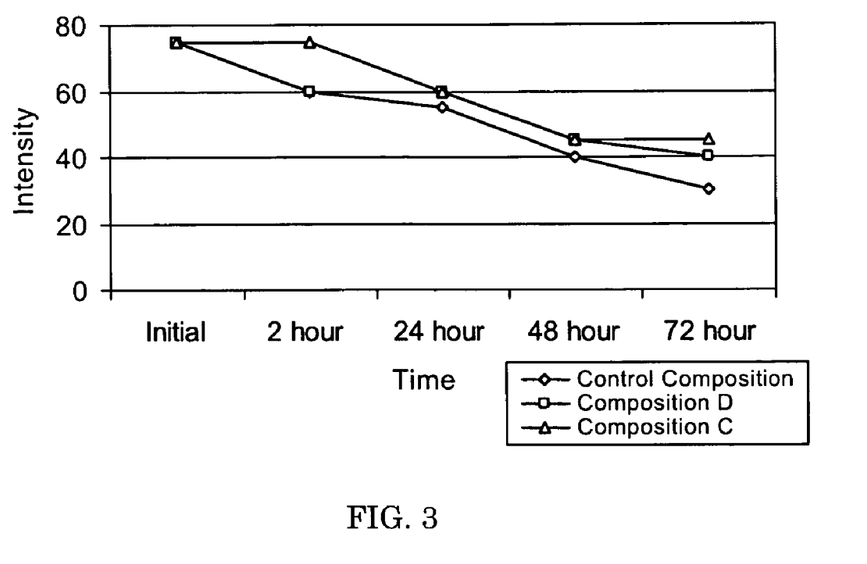
FIG. 3 is a line graph illustrating the fragrance intensity over time of a second embodiment of three fresh perfume compositions (the compositions include a control perfume composition and two perfume compositions made in accordance with the present invention)

In this example, two more deodorizing compositions for inanimate surfaces (e.g. rugs, clothing, counter tops, etc.) are evaluated in 800 ml plastic bottles, constructed of 52 g of HDPE (100% by weight of the bottle), for preserving perfume integrity or minimizing loss of fragrance. The first composition, Composition C, is approximately 0.065% perfume, made up of at least about 47.9% perfume ingredients having a Clog P less than about 3 and a boiling point greater than about 280° C. The second composition, Composition D is approximately 0.065% perfume, made up of about 34.4% perfume ingredients having a Clog P less than about 3 and a boiling point greater than about 280° C. The control perfume is approximately 0.05% perfume of which 18.7% are perfume ingredients having a Clog P of less than 3 and a boiling point greater than about 280° C. Panelists evaluate the fresh and aged perfumes according to the steps identified in Example I. FIG. 3 and Table 7 show the intensity of the fresh compositions on fabric over time.

TABLE 7

| FRESH PERFUME | Wet fabric | 2 hour Dry | 24 hour Dry | 48 hour Dry | 72 hour Dry |
|---|---|---|---|---|---|
| Control Composition | 75 | 60 | 55 | 40 | 30 |
| Composition D | 75 | 60 | 60 | 45 | 40 |
| Composition C | 75 | 75 | 60 | 45 | 45 |

Figure 4:
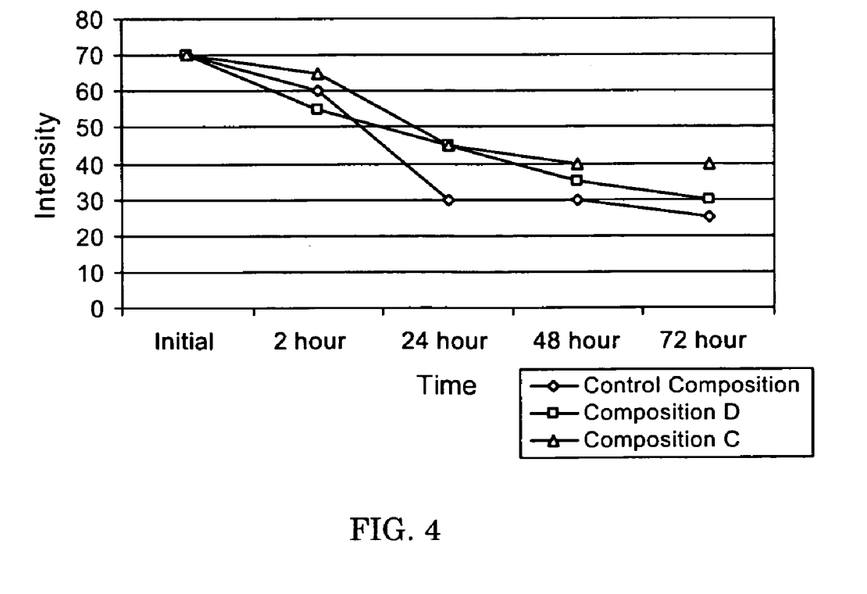
FIG. 4 is a line graph illustrating the fragrance intensity over time of the same three perfumes illustrated in FIG. 3 but aged (subject to ambient temperatures or a 49° C. room for about two weeks or more).

FIG. 4 and Table 8 show the fragrance intensity of the aged compositions over time.

TABLE 8

| AGED PERFUME | Wet fabric | 2 hour Dry | 24 hour Dry | 48 hour Dry | 72 hour Dry |
|---|---|---|---|---|---|
| Control Composition | 70 | 60 | 30 | 30 | 25 |
| Composition D | 70 | 55 | 45 | 35 | 30 |
| Composition C | 70 | 65 | 45 | 40 | 40 |

At 72 hours, character comments included "character noticeability and fits target" for Composition D and "more floral citrus" for Composition C.

EXAMPLE III

An aqueous composition suitable for use in the invention is formulated as follows.

| Components: | Wt. % |
|---|---|
| DI Water | 94.968 |
| Ethanol | 3.000 |
| Diethylene Glycol | 0.250 |
| Surfactant | 0.100 |
| Uniquat 2250 | 0.060 |
| Basophor ELH60 | 0.050 |
| Triethanolamine | 0.300 |
| Perfume | 0.250 |
| Hydroxypropyl Beta Cyclodextrin | 0.900 |
| Koralone B-119 | 0.015 |
| Citric Acid | 0.100 |
| 5% NaOH | 0.007 |
|  | 100.000 |

The aqueous composition is stored in HDPE containers for about 8 weeks at ambient temperature. After storage, gas chromatography analysis is used to determine the amount of the perfume ingredients in table 9 which are remaining in the composition. Approximate loss is calculated based on the amount of each ingredient originally present.

TABLE 9

| Perfume Ingredients with Clog P < 3 | Perfume Ingredients with Clog P > 3 |
|---|---|
| Oxane | Allyl Caproate |
| Carvone | Neral |
| Methyl phenyl carbinyl acetate | Geranial |
| Methyl dihydro jasmonate | Citronellyl nitrile |
| Ligustral | Dihydro myrcenol |
| Diethyl phthalate | Geraniol |
| Cumin aldehyde | Citronellal |
|  | Tetrahydro linalool |
|  | 3-Decanone |
|  | Floralozone |
|  | Flor acetate |
|  | Bourgeonal |
|  | beta-ionone |
|  | gamma-damascone |
|  | alpha-damascone |

TABLE 9-continued

| Perfume Ingredients with Clog P < 3 | Perfume Ingredients with Clog P > 3 |
|---|---|
| | Verdox |
| | Vertenex |
| | Decanal |
| | Sabinene |
| | Undecavertol |
| | Frutene |
| | Gamma-terpinene |
| | beta-pinene |
| | 2-Methyl heptenone |
| | alpha-pinene |
| | delta-3-carene |
| | alpha-terpinene |
| | Allo ocimene |
| | Ethyl decanoate |
| | Tangerinol |
| | Isopropyl myristate |

The average percent loss is less than 50% for perfume ingredients with a Clog P less than 3 and greater than 70% for perfume ingredients with a Clog P greater than 3. This example demonstrates that perfume ingredients with a Clog P greater than 3 undergo significant loss when stored in HDPE containers.

EXAMPLE IV

A liquid fabric softener in accordance with the present invention is made according to the following formula and is packaged in HDPE containers.

| Ingredient | Parts |
|---|---|
| di(hydrogenated tallow)dimethyl ammonium chloride | 5.25 |
| Perfume of Example III | 1.00 |
| Water | To 100 |

EXAMPLE V

A liquid laundry detergent of the present invention is made to the following formula and is packaged in containers having an inner surface of fluorinated polyethylene.

| Ingredient | Parts |
|---|---|
| K/Na C13 linear alkylbenzene sulfonate | 7.2 |
| K/Na C14-15 alkyl polyethoxylate(2.25) sulfonate | 10.8 |
| C12-13 alcohol poly(6.5)ethoxylate | 6.5 |
| C12 alkyltrimethyl ammonium chloride | 1.2 |
| C12-14 fatty acid | 13.0 |
| Oleic acid | 2.0 |
| Citric acid (anhydrous) | 4.0 |
| Diethylenetriamine pentaacetic acid | 0.23 |
| Enzyme | 0.91 |
| Ethoxylated tetraethylene pentamine(15-18 mol. EO at each H) | 1.5 |
| Monoethanolamine | 2.0 |
| Propylene glycol | 7.25 |
| Ethanol | 7.75 |
| Formic acid | 0.66 |
| Calcium ion | 0.03 |
| Composition of Example III | 0.65 |
| Water and minors | To 100 |

The dimensions and values disclosed herein are not to be understood as being strictly limited to the exact numerical values recited. Instead, unless otherwise specified each such dimension is intended to mean both the recited value and a functionally equivalent range surrounding that value. For example, a value disclosed as "10%" is intended to mean "about 10%". Further, all percentages are intended to mean weight percent unless otherwise specified.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such chances and modifications that are within the scope of this invention.

What is claimed is:

1. An aqueous household cleaning, fabric treatment, or deodorizing product comprising:
    a. an aqueous composition comprising:
        i. from about 0.1 wt. % to about 30 wt. % of a surfactant; and
        ii. from about 0.003 wt. % to about 5 wt. % of a perfume, wherein at least about 40 wt. % of said perfume is one or more hydrophilic perfume ingredients selected from the group consisting of: ethyl vanillin; isoeugenyl acetate; heliotropine diethyl acetal; 2H-1,5-benzodioxepin-3(4H)-one, 7-methyl-; 4-(4-hydroxyphenyl)butanone-2; vanillin isobutyrate; helional; cashmeran; piperonyl acetone; methyl beta-naphthyl ketone; methyl dihydrojasmonate; lyral; and mixtures thereof; and
    b. a plastic container constructed of at least about 80 wt. % of HDPE, wherein said product is contained in said plastic container.

2. The product of claim 1 wherein said perfume contains at least about 70 wt. % of one of more hydrophilic perfume ingredients.

3. The product of claim 1 wherein said product further comprises a substrate, said substrate is impregnated with said aqueous composition.

4. The product of claim 3 wherein said substrate is a nonwoven wet-wipe.

5. The product of claim 1 wherein said aqueous composition comprises from about 0.05 wt. % to about 0.2 wt. % of said perfume.

6. The product of claim 1 wherein said aqueous composition further comprises cyclodextrin.

7. A method of preserving perfume integrity and extending fragrance life in household cleaning, fabric treatment or deodorizing products comprising:
    a. providing an aqueous composition comprising from about 0.1 wt. % to about 30 wt. % of a surfactant, and from about 0.003 wt. % to about 5 wt. % of a perfume, wherein said perfume contains at least about 40 wt. % of one or more hydrophilic perfume ingredients selected from the group consisting of:

ethyl vanillin; isoeucienyl acetate, heliotropine diethyl acetal; 2H-1,5-benzodioxepin-3(4H)-one, 7-methyl-; 4-(4-hydroxyphenyl)butanone-2; vanillin isobutyrate; helional; cashmeran; piperonyl acetone; methyl beta-naphthyl ketone; methyl dihydrojasmonate; lyral; and mixtures thereof; and b. packaging said product in a plastic container constructed of at least about 80 wt. % hydrophilic perfume compatible materials.

8. The method of claim 7 wherein said product further comprises a substrate, said substrate is impregnated with said aqueous composition.

* * * * *